United States Patent [19]

Cochrum

[11] Patent Number: 4,696,286
[45] Date of Patent: Sep. 29, 1987

[54] COATED TRANSPLANTS AND METHOD FOR MAKING SAME

[75] Inventor: Kent C. Cochrum, Corte Madera, Calif.

[73] Assignee: The Regents of the University of California, Berkeley, Calif.

[21] Appl. No.: 866,167

[22] Filed: May 22, 1986

Related U.S. Application Data

[63] Continuation-in-part of Ser. No. 711,664, Mar. 14, 1985, abandoned.

[30] Foreign Application Priority Data

Mar. 7, 1986 [NO] Norway ............... 860858

[51] Int. Cl.$^4$ ............................................. A61B 19/00
[52] U.S. Cl. ...................................... 128/1 R; 435/1; 435/182
[58] Field of Search ............... 3/1; 128/1 R; 435/182, 435/1, 240, 241

[56] References Cited

U.S. PATENT DOCUMENTS

| | | | |
|---|---|---|---|
| 3,629,390 | 12/1971 | Wentworth | 424/2 |
| 3,682,776 | 8/1972 | Grundmann et al. | 195/1.7 |
| 4,120,649 | 10/1978 | Schechter | 8/94.11 |
| 4,251,387 | 2/1981 | Lim | 252/316 |
| 4,352,883 | 10/1982 | Lim | 435/178 |
| 4,353,888 | 10/1982 | Sefton | 424/25 |
| 4,391,909 | 7/1983 | Lim | 435/178 |
| 4,407,957 | 10/1983 | Lim | 435/178 |
| 4,409,331 | 10/1983 | Lim | 435/178 |
| 4,439,521 | 3/1984 | Archer | 435/1 |

FOREIGN PATENT DOCUMENTS

| | | | |
|---|---|---|---|
| 1215922 | 12/1986 | Canada . | |
| 0051237 | 5/1981 | Japan | 435/182 |
| 0018179 | 1/1985 | Japan | 435/1 |

OTHER PUBLICATIONS

W. J. Tze & J. Tai; Transplantation Proceedings, (1982), 14 (4):714–723.
Anthony M. Sun et al.; Diabetes, (1977), 26:1136–1139.
G. F. Klomp; Trans Am Soc Artif Intern Organs, (1979), 25:74–76.
F. V. Lamberti et al.; Abstract Paper American Chem Society, (1983), 85:162.
F. V., Lamberti et al.; Artificial Organs, (1984), 8:112.
Franklin Lim; Science, (1980), 210:908–910.
Franklin Lim & Richard Moss; Journal of Pharm Sciences, (1981), 70:351–354.
Yin F. Leung et al.; Artificial Organs, 7(2):208–212.
Harrison's Principles of Internal Medicine; 10th Edition, McGraw Hill; New York; 1983, pp. 668–669.
Kulkarni et al.; Arch Surg, (1966) 93:839–843.

Primary Examiner—C. Fred Rosenbaum
Assistant Examiner—Jerome R. Smith, Jr.
Attorney, Agent, or Firm—Ciotti & Murashige, Irell & Manella

[57] ABSTRACT

Transplants, such as pancreatic islets, are made suitable for transplantation into a genetically dissimilar individual by coating the transplant with a surface-conforming bonding bridge layer of a multifunctional material that binds chemically to a surface component of the transplant followed by a semipermeable, biologically compatible layer of a polymer that binds chemically to the bonding bridge layer.

16 Claims, No Drawings

COATED TRANSPLANTS AND METHOD FOR MAKING SAME

CROSS-REFERENCE TO RELATED APPLICATION

This application is a continuation-in-part of copending application U.S. Ser. No. 711,664, filed Mar. 14, 1985 now abandoned.

FIELD OF THE INVENTION

This invention is in the field of medical transplants. More particularly it relates to solid organ transplants, such as pancreatic islets, that have been coated with an immunological barrier to render them suitable for transplantation.

BACKGROUND ART

Transplants between genetically dissimilar individuals (called xenografts when the doner and host are of different species or allografts when the doner and host are of the same species) normally induce an immune response in the host individual. The immune response often leads to rejection or destruction of the transplant or, if the transplant contains immunocompetent cells, to graft-versus-host disease (GVHD).

Various techniques have been used to attempt to reduce or eliminate the immunogenicity of transplants. For instance, transplants have been manipulated by culturing under conditions that cause selective elimination or deactivation of cells that stimulate the immune response or by treating the transplant with antisera that recognize receptors on such cells. *Transplantation Proceedings* (1982) 14(4):714–723. Pancreatic islets have also been placed in semipermeable polymeric containers, called "diffusion pouches" in attempts to make an artificial pancreas. *Diabetes* (1977) 26:1136–9 and *Trans Am Soc Artif Intern Organs* (1979) 25:74–76.

A series of patents—U.S. Pat. Nos. 4,352,883, 4,391,909, 4,407,957, and 4,409,331—relate to pancreatic islets that are encapsulated in droplet-shaped capsules by initially entrapping the islets in a polysaccharide (e.g., alginate) gel, and then cross-linking the surface of the gel with a polycationic (e.g., polylysine) polymer. Applicant believes that the polysaccharide used in this procedure has no affinity for the islet surface and, indeed, is repelled by the surface of the islets. This increases the likelihood of having holes or gaps in the entrapping gel and failure to encapsulate the islets entirely.

*Abst Pap Am Chem Soc* (1983) 185:162, *Artificial Organs* (1984) 8:112, and U.S. Pat. No. 4,353,888 report encapsulation of blood cells in acrylate polymers and suggest the same might be done with other cells such as pancreatic islets.

DISCLOSURE OF THE INVENTION

One aspect of the invention is a transplant suitable for transplantation into a genetically dissimilar individual said transplant being coated with an immunological barrier membrane that conforms to the surface of the transplant, said membrane comprising a noncytotoxic inner layer that is bonded chemically to the surface of the transplant and an outer biologically compatible, water-insoluble semipermeable layer bonded chemically to the inner layer.

Another aspect of the invention is a method of treating a transplant to make it suitable for transplantation into a genetically dissimilar individual comprising:
(a) coating the transplant with a first layer of a noncytotoxic material that forms a chemical bond with the surface of the transplant, said first layer conforming to the surface of the transplant; and
(b) coating the transplant with a second layer of a polymeric material that forms a chemical bond with the material of the first layer, said second layer being biologically compatible and semipermeable.

MODES FOR CARRYING OUT THE INVENTION

The term "transplant" is intended to denote one or a multiplicity of mammalian cells or a multiplicity of associated mammalian cells that define an organelle or organ from a doner mammal or doner mammals that is (are) genetically dissimilar (xenogeneic or allogeneic) to the intended recipient. It will typically be used to denote endocrine (pituitary, thyroid, adrenal, parathyroid, pancreas) cells, organelles, or glands but may also be used in other organ transplants such as heart, liver, lung and kidney transplants.

The term "noncytotoxic" is intended to mean that a material does not substantially affect the viability and/or functionality of the cell, organelle, or organ to which the material is applied.

The phase "bonded chemically" is intended to indicate the existence of one or more covalent, ionic, and/or hydrogen bonds.

The phrase "biologically compatible" means that the indicated layer is substantially nonantigenic relative to the immune system of the recipient and does not induce a foreign body (fibrosis) reaction.

The term "semipermeable" means that the indicated layer permits inward diffusion of low molecular weight cell, organelle, or organ nutrients, as the case may be, an outward diffusion of metabolic products but prevents inward or outward diffusion of compositions that may cause deleterious effects to the transplant or recipient.

The present invention is applicable to a variety of transplants and is not intended to be limited to a particular type of cell, organelle, or organ or to a particular mammalian species. Accordingly, while the invention is described and exemplified below with respect to xenogeneic and allogeneic pancreatic islets of various animals, it will be appreciated that these teachings may be extended to other tissues of other mammalian species, including humans.

Pancreatic tissue may be obtained and cultured using known techniques to render it suitble for coating in accordance with the invention. The tissue is obtained fresh and divided by mincing, teasing, comminution, and/or mild digestion with collagenase to facilitate separation of the islets from contaminating cells and materials. The islets may be isolated from the divided/digested pancreatic tissue by washing, filtering, centrifuging or picking procedures. Preferably, the isolate is cultured in a liquid culture medium under conditions and for a time that causes antigenic components (e.g., passenger leukocytes) in the isolate to be deactivated or eliminated. Such media and conditions are described in *Transplant Proc* (1982) 14(4):714–23.

The purified isolated islets are then coated with a layer of a noncytotoxic polyfunctional material that has a high affinity for one or more islet cell surface components. The term "polyfunctional" means that the material has two or more available sites for facile interaction with the surface components of the cell, on the one hand, and functional groups of the outer layer material, on the other hand. The polyfunctional material acts as a bonding bridge between the cell surface and the outer polymeric layer—forming stable (in terms of susceptibility to breakage during the coating process, subsequent storage, if any, and after transplantation) chemical bonds with one or more cell surface components (e.g., depending on the nature of the material, reactive groups of proteins, carbohydrates, or lipids) and with functional groups of the polymeric material that forms the outer, semipermeable layer. The material may be synthetic or natural, inorganic or organic. Examples of materials that may be used to form the inner coating are: aluminum hydroxide; disaccharides (maltose, sucrose, lactose, and trehalose or sulfated derivatives thereof); low molecular weight, nonpolymeric protein coupling or cross-linking agents such as bifunctional disulfides such as 3,3'-dimethyldithiobispropionate (DTBP) and N-succinimidyl-3-(2-pyridyldithio) propionate (SPDP), N-hydroxysuccinimido esters of 6-maleimidocaproic acid, 2-bromoacetic acid, and 2-iodoacetic acid, other active esters of such acids, imidoesters such as dimethyladipimidate, and dissuccinimidyl suberate, aldehydes such as glutaraldehyde, bis-azido compounds such as bis (p-azidobenzoyl) hexanediamine, bis-diazonium derivatives, diisocyanates such as bis-tolylene-2,6-diisocyanate, and carbodiimides; immunoglobulin to a surface component of the transplant, such as antibodies to class I or class II MHC antigens; lectins (i.e., plant proteins that bind to sugar or sugar residues) such as concanavalin A, DBA, soybean agglutinin, wheat germ agglutinin, and phytohemagglutinin; and polyionic polyamino acids that have a charge opposite to the surface charge of the transplant surface, e.g., pancreatic islets have a negative surface charge and a polycationic polyamino acid such as polylysine may be bonded to the islet surface.

The manner in which the bonding bridge material is applied to the surface of the transplant will depend upon the nature of the material. It will typically be applied as an aqueous suspension or solution under conditions (physiological pH, i.e., 7–7.5, temperature, i.e., about 37° C., and ionic strength) that promote and permit uniform coating of the surface and the formation of stable, chemical bonds between the material and the given cell surface component(s). The application will normally be effected by contacting the transplant with the suspension or solution with mild agitation for about 4 to 20 min. The coating is preferably applied as a thin, surface-conforming layer one or a few molecules in thickness.

The outer layer is made from a polymer that will provide the requisite semipermeability and immunological compatibility. Polyamino acids that have reactive carboxyl, amino or imino groups, such as polyaspartic acid, polyglutamic acid, polylysine, and polyarginine are preferred, with the particular polyamino acid depending on the nature and charge of the available bonding sites of the inner coating. For instance, if the available sites are negatively charged a polycationic polyamino acid such as polylysine is used. Vice versa, if the available sites are positively charged a polyanionic polyamino acid such as polyaspartic acid may be used. The permeability of the layer is primarily a function of the molecular weight of the material and the thickness of the layer. Permeability increases with increasing molecular weight and decreases with increasing thickness. The molecular weight of the polymer will typically be in the range of 5,000 to 300,000 daltons, and the thickness will usually range between 0.1–10 microns, more usually 0.1–3 microns. These polymers may be applied to the transplants in dilute aqueous solutions (0.1% to 1% by weight) at physiological pH, ionic strength and temperature. The contacting of the polymer solution with the transplant will typically be done with mild agitation (to ensure complete coating) for about 4 to 10 min per layer. If desired, the outer layer may be formed as a plurality of coats of the same or different polymer. One or more intermediate layers of innocuous materials, such as polysaccharides, may be used, provided they (1) do not disrupt the chemical bonding of the inner layer to the transplant surface, (2) do not affect adversely the viability or functionality of the transplant, and (3) provide a suitable substrate to which the outer, semipermeable layer may be bonded chemically.

The following examples further illustrate the transplants and the materials and methods used to form the inner and outer coatings of the transplants. These examples are not intended to limit the invention in any manner.

PANCREATIC ISLET ISOLATION

Fresh pancreatic tissue was comminuted and placed in Hank's solution containing collagenase to digest connective tissue. The resulting digest was subjected to Ficoll-Hypaque gradient centrifugation to isolate the islets. The isolated islets were cultured for 7 days at 37° C. in RPMI 1640 medium supplemented with 10% fetal calf serum under a moist 5% $CO_2$ atmosphere.

ISLET COATING

A. Aluminum Hydroxide

Isolated islets are suspended in 3 ml RPMI 1640 at a concentration of $10^3$ islet per ml. Aluminum hydroxide (Sigma Chemical Company) is ground in a mortar and pestle until the gel particle size is 1–3 microns. A one percent $Al(OH)_3$ solution is made in physiological saline. The RPMI medium is removed from the islet and replaced with 3 ml of the 1% $Al(OH)_3$ saline solution. The islet-$Al(OH)_3$ solution is mixed by rotation for 2.5 min. The $Al(OH)_3$-coated islets are sedimented out and the excess $Al(OH)_3$ solution removed. The coated islets are then washed 3 times in 6 ml physiological saline, pH 7.

The coated islets are then transferred to 3 ml of a 0.5% physiological saline, pH 7 solution of poly-L-aspartic acid, mw 50,000 (Sigma Chemical Company) and mixed for 4 min. The poly-L-aspartic is removed and the coated tissue islets washed 3 times with 6 ml of physiological saline, pH 7.

The coated islets are then suspended in 3 ml of 0.5% solution of poly-L-lysine, mw 50,000 (Sigma Chemical Company) and mixed for 5 min. The poly-L-lysine is removed and the islets are washed 3 times in physiological saline, pH 7.

The poly-L-aspartic acid and poly-L-lysine coatings and washes may be repeated if a thicker outer layer is desired.

Following the final physiological saline wash the coated islets are suspended in 10 ml of a 1% solution of deferoxamine (Ciba-Geigy) in physiological saline, pH 7.2 for 10 min. The deferoxamine treatment is repeated for another 10 min and then removed. The coated islets are washed 2 times in physiological saline and RPMI 1640 media. The islets can be transplanted at this point or returned to tissue culture. The coated islets can be maintained in tissue culture in RPMI 1640, 10% fetal calf serum, 5% $CO_2$, 85% air.

B. DTBP

One thousand isolated islets are suspended in 0.5% DTBP in 3 ml physiological saline, pH 7.2. The islets are mixed for 30 sec and then 30 ml of saline are added to the suspension and the DTBP-coated islets are allowed to settle out. The DTBP solution is removed and the islets washed 3 times with 20 ml saline, pH 7. The final saline wash is removed and 3 ml of a 0.5% poly-L-aspartic solution, mw 50,000 (Sigma Chemical Company) is added and mixed for 4 min.

The poly-L-aspartic is removed and the polymer-coated islets are washed 3 times with 6 ml of saline. The coated islets are then suspended in 3 ml of 0.5% poly-L-lysine, mw 50,000 (Sigma Chemical Company) and mixed for 5 min. The polymer-L-lysine is removed and the islets washed 3 times in physiological saline.

C. MHC Antiserum

One thousand isolated rat islets are suspended in 0.25 ml of Class I histocompatability antiserum (M. A. Bioproducts) diluted 1/2 with physiological saline, pH 7.5. The islets and antibody are incubated at 4° C. for 45 min. The antibody coated tissue is then washed 2 times with 5 ml physiological saline, pH 7. The final saline wash is removed and 3 ml of 0.5% poly-L-lysine, mw 50,000 (Sigma Chemical Company) and mixed for 5 min. The poly-L-lysine is removed and the islets washed in physiological saline, pH 7. The coated islets are then suspended in 3 ml of a 0.5% poly-L-aspartic solution, mw 50,000 (Sigma Chemical Company) and mixed for 4 min. The poly-L-aspartic is removed and the islets are washed in physiological saline, pH 7. If desired the islets can be coated a second time with poly-L-lysine and washed. An alternate coating method is to biotinylate the bridging antibody and polymer and utilize the standard biotin-avidin system.

Human islets may be coated in a similar manner using available antibodies to human Class I/II MHC antigens.

D. Lectin

One thousand isolated islets are suspended in 10 μg/ml Con A in 3 ml physiological saline, pH 7 (Sigma Chemical Company). The islets are mixed for 15 min at 4° C. and washed with 10 ml physiological saline, pH 7. The saline is removed and replaced with 3 ml of 0.5% poly-L-lysine, mw 50,000, saline solution, pH 7, and mixed for 5 min. The poly-L-lysine is removed and the islets washed in physiological saline, pH 7. The coated islets are then suspended in 3 ml of a 0.5% poly-L-aspartic acid, mw 50,000 (Sigma Chemical Company) solution, and mixed for 4 min. The islets are then washed in physiological saline, pH 7. A second coating of poly-L-lysine may be added if desired.

An alternate coating method is to biotinylate the lectin bridge and polymer and utilize the standard biotin-avidin system.

E. Polycationic Polyamino Acid

Isolated islets are suspended in 3 ml of a 0.5% physiological saline, pH 7, solution of poly-L-lysine, mw 50,000, and mixed for approximately 10 min. The poly-L-lysine solution is then removed and the coated islets washed 3 times with 6 ml of physiological saline.

The coated islets are then transferred to 3 ml of a 0.5% physiological saline solution of poly-L-aspartic acid, mw 50,000, and mixed for approximately 10 min. The poly-L-aspartic is removed and the coated islets are again washed 3 times with saline.

Finally, the coated islets are again suspended in 3 ml of the 0.5% saline solution of poly-L-lysine, and mixed for approximately 10 min. followed by washing in saline.

IN VITRO TESTING OF ISLETS

Functional viability and regulation by glucose were determined for the coated islets. They were coated using methods given in Examples A–E. The immunoreactive insulin (IRI) concentration of the tissue culture medium was determined by radioimmunoassay. Insulin secretion was determined in response to one-hour sequential stimulation with 2 mM glucose and 25 mM glucose. Insulin secretion from 60 coated islets in 5 ml RPMI medium was determined. Little insulin was secreted in response to 2 mM glucose (nonstimulating concentration). In response to 25 mM glucose the treated islets secreted insulin at 1.5–2.2 mg/islet/hr. This is comparable to the response insulin secreted by fresh, untreated islets.

IN VITRO TESTING OF ISLETS

Balb/C mice were made diabetic by the intraperitoneal injection of streptozotocin (180 mg/kg body weight). Nonfasting plasma glucose levels ranged 400–600 mg/dL. Only mice with plasma glucose concentrations greater than 400 mg/dL for two weeks received transplants. Isolated rat (Sprague-Dawley) islets were coated, using methods given in Examples A-D. Two thousand coated islets were transplanted intraperitoneally into each diabetic mouse, and non-fasting plasma glucose levels were determined three times a week. Plasma glucose level dropped to 100–175 mg/dL in the transplanted mice. These coated islets have maintained normoglycemia in the transplanted mice for three weeks to one and a half years. Normoglycemic mice were sacrificed after three months in order to recover the transplanted islets. The coated islets showed no gross or histological tissue reaction, and the recovered islets were viable and capable of in vitro regulation by glucose.

A dog was made diabetic by total pancreatectomy. Following surgery her initial blood glucose level was 430 mg/dL. and she required 15 U of NPH insulin to keep it below 300 mg/dL. Five thousand islets were obtained from an unrelated dog's pancreas, treated using the MHC antiserum method (Example C above, anti dog MCH antisera may be obtained from Microbiological Associates) and transplanted into the peritoneal cavity of the diabetic dog. After transplantation her blood glucose level and insulin requirements declined within 24 hours. The transplanted islets have continued to function for over 2½ years. The dog requires no immunosuppressive drugs, and she has a blood glucose level of from 170–250 without insulin, lower than the pretransplant level, but above that of normal, nondiabetic dogs. This slightly higher than normal level was expected, since only 5,000 islets were transplanted. (A normal pancreas contains approximately 300,000 islets and approximately 20,000 would restore this dog to normoglycemia.) The dog is maintained on 6 U NPH insulin (to encourage development and multiplication of the islets) and has a blood glucose of 93 mg/dL. She has showed no clinical signs of diabetes.

Modifications of the above described modes for carrying out the invention that are obvious to persons of skill in the fields of medicine, immunology, biochemistry and/or related fields are intended to be within the scope of the following claims.

I claim:

1. A transplant suitable for transplantation into a genetically dissimilar individual, said transplant being coated with an immunological barrier membrane that conforms to the surface of the transplant, said membrane comprising a noncytotoxic inner layer that is bonded chemically to the surface of the transplant, and an outer, biologically compatible, water-insoluble semipermeable layer bonded chemically to the inner layer, wherein the inner layer is comprised of a material selected from the group consisting of:
 (a) aluminum hydroxide;
 (b) a disaccharide;
 (c) a polyfunctional cross-linking agent;
 (d) an immunoglobulin to a surface component of the transplant;
 (e) a lectin; and
 (f) a polyionic polyamino acid having an opposite charge to that of the transplant surface; and the outer layer is comprised of a polyamino acid that has reactive carboxyl, amino or imino side groups.

2. The transplant of claim 1 wherein said transplant is an endocrine transplant.

3. The transplant of claim 1 wherein said transplant is a pancreatic islet.

4. The transplant of claim 1 wherein the inner layer is comprised of a material selected from the group consisting of a bifunctional disulfide, an immunoglobulin that binds to a MHC antigen of the transplant, concanavalin A and polylysine.

5. The transplant of claim 1 wherein the polyamino acid of the outer layer is polylysine, polyarginine, polyaspartic acid, or polyglutamic acid.

6. The transplant of claim 5 wherein the molecular weight of the polyamino acid of the outer layer is in the range of 5,000 to 300,000 daltons and the thickness of the outer layer is between 0.1 and 10 microns.

7. The transplant of claim 3 wherein the inner layer is composed of aluminum hydroxide and the outer layer is composed of a first layer of polyaspartic acid chemically bound to the aluminum hydroxide and a second layer of polylysine chemically bound to the first layer.

8. The transplant of claim 1 wherein at least one intermediate layer of innocuous material is interposed between the inner and outer layers and the outer layer is bonded chemically to the contiguous intermediate layer.

9. A method of treating a transplant to make it suitable for transplantation into a genetically dissimilar individual comprising:

coating the transplant with a first or inner layer of a noncytotoxic material that forms a chemical bond with the surface of the transplant, said first layer conforming to the surface of the transplant, said first layer comprised of a material selected from the group consisting of
 (a) aluminum hyhdroxide;
 (b) a disaccharide;
 (c) a polyfunctional cross-linking agent;
 (d) an immunoglobulin to a surface component of the transplant;
 (e) a lectin; and
 (f) a polyionic polyamino acid having an opposite charge to that of the transplant surface; and coating the transplant with a second or outer layer of a polymeric material that forms a chemical bond with the material of the first layer, said second layer being biologically compatible and semipermeable, said second layer comprising a polyamino acid that has reactive carboxyl, amino or imino side groups.

10. The method of claim 9 wherein said transplant is an endocrine transplant.

11. The method of claim 9 wherein said transplant is a pancreatic islet.

12. The method of claim 9 wherein the inner layer is comprised of a material selected from the group consisting of a bifunctional disulfide, an immunoglobulin that binds to a MHC antigen of the transplant, concanavalin A and polylysine.

13. The method of claim 9 wherein the polyamino acid of the outer layer is polylysine, polyarginine, polyaspartic acid, or polyglutamic acid.

14. The method of claim 13 wherein the molecular weight of the polyamino acid is in the range of 5,000 to 300,000 daltons and the thickness of the outer layer is between 0.1 and 10 microns.

15. The method of claim 11 wherein the inner layer is composed of aluminum hydroxide and the outer layer is composed of a first layer of polyaspartic acid chemically bound to the aluminum hydroxide and a second layer of polylysine chemically bound to the first layer.

16. The method of claim 9 wherein the transplant is coated with at least one intermediate layer of innocuous material interposed between the first layer and the second layer, with the second layer being bonded chemically to the contiguous intermediate layer.

* * * * *